United States Patent [19]

Roskott et al.

[11] 4,158,021

[45] Jun. 12, 1979

[54] PROCESS FOR THE PREPARATION OF A COPOLYMERIZABLE COMPOSITION

[75] Inventors: Lodewijk Roskott, Gorssel; Arnold Schroeder, Deventer, both of Netherlands

[73] Assignee: Akzona Incorporated, Asheville, N.C.

[21] Appl. No.: 855,092

[22] Filed: Nov. 25, 1977

Related U.S. Application Data

[62] Division of Ser. No. 588,993, Jun. 29, 1975, Pat. No. 4,097,467.

[30] Foreign Application Priority Data

Jun. 21, 1974 [NL] Netherlands .......................... 7408353

[51] Int. Cl.$^2$ ..................... C07C 179/06; C08L 67/06
[52] U.S. Cl. ..................................... 568/567; 252/426; 252/186; 260/861; 568/563
[58] Field of Search ............... 260/610 C, 610 R, 861; 252/426, 186

[56] References Cited

U.S. PATENT DOCUMENTS

| | | |
|---|---|---|
| 3,592,874 | 7/1971 | Reese et al. ..................... 260/75 UA |
| 3,853,967 | 12/1974 | Leveskis ................................. 260/861 |
| 3,945,940 | 3/1976 | Leveskis ................................. 252/186 |

FOREIGN PATENT DOCUMENTS

954600 4/1964 United Kingdom.

Primary Examiner—Walter C. Danison
Attorney, Agent, or Firm—Francis W. Young; Robert F. Green

[57] ABSTRACT

A copolymerizable composition containing an unsaturated polyester resin and a metal accelerator, suitable for copolymerization with an ethylenically unsaturated monomer, has incorporated therein as a peroxide initiator composition an alkylaldehyde peroxide which may be unsubstituted, or alkyl- or aryl-substituted, the alkylaldehyde peroxide containing not more than 20 carbon atoms and at least 1.5 active oxygen atoms per carbonyl group of said alkylaldehyde.

8 Claims, No Drawings

PROCESS FOR THE PREPARATION OF A COPOLYMERIZABLE COMPOSITION

This is a division, of application Ser. No. 588,993, filed June 29, 1975, now U.S. Pat. No. 4,097,467.

BACKGROUND OF THE INVENTION

Process for the preparation of a copolymerizable composition.

The invention relates to a process for the preparation of a copolymerizable composition and to a process for the preparation of a peroxide composition to be used in the copolymerization of said copolymerizable composition.

By unsaturated polyester resins are to be understood solutions of unsaturated polyesters in reactive monomers and one or more polymerizable $CH_2=C<$ groups such as styrene, vinyl toluene, methyl methacrylate, diallyl phthalate and divinyl benzene.

The ratio monomer to unsaturated polyester is generally 30–50% by weight of monomer to 70–50% by weight of polyester.

The unsaturated polyester is obtained by reaction of approximately equivalent amounts of a polyvalent alcohol such as ethylene glycol, propylene glycol, diethylene glycol and an unsaturated dibasic carboxy acid such as maleic acid, fumaric acid, itaconic acid in the presence, if desired, of a saturated acid such as phthalic acid, isophthalic acid, tetrachlorophthalic acid, malonic acid, adipinic acid, sebacinic acid, succinic acid and the like.

In order to improve the stability of the unsaturated polyester, inhibitors are incorporated in them in amounts ranging from 0.001 to 0.003% by weight. The most commonly used inhibitors are hydroquinone, quinone and para tert. butyl catechol.

The above-described unsaturated polyester resins may be copolymerized at room temperature under the influence of organic peroxides yielding free radicals and in the presence of one or more accelerators for the peroxide used.

The British patent specification No. 954,600 describes the use of particular aldehyde peroxides as initiators in combination with a cobalt compound and a secondary amine in the copolymerization of unsaturated polyester resins at room temperature.

These aldehyde peroxides are obtained by condensation of an aldehyde with hydrogen peroxide under reaction conditions which are not specified. The impression is given, however, that the reaction must be so conducted that the condensation product preferably contains 1-hydroxy-1-alkylhydroperoxide and bis(1-hydroxy alkyl) peroxide. These peroxides may be regarded as aldehyde peroxides which contain respectively 1 active oxygen atom and ½ active oxygen atom per carbonyl group of the aldehyde used in the preparation of the peroxide. It is recommended that in practice the copolymerization of unsaturated polyester resins should be carried out using a combination of bis(1-hydroxy heptyl) peroxide and a cobalt accelerator. Unsaturated polyester resins in which such a combination is incorporated have a short gel time, which meets with practical drawbacks.

DESCRIPTION OF THE INVENTION

It has now been found that it is possible to obtain a copolymerizable composition which not only rapidly cures but also has a gel time acceptable in practice if in a copolymerizable unsaturated polyester resin which already contains a metal accelerator there is incorporated a peroxide composition which substantially consists of an alkyl aldehyde peroxide substituted or not with alkyl groups or aryl groups, which alkyl aldehyde peroxide contains not more than 20 C-atoms and has at least 1½ active oxygen atoms per carbonyl group of the alkyl aldehyde used for the preparation of the peroxide composition.

The peroxide composition to be used according to the invention may be incorporated in the unsaturated polyester resin in amounts ranging from 0.1 to 10% by weight, and preferably from 3 to 7% by weight, calculated on the unsaturated polyester resin. It can be incorporated in it as such. For reasons of safety, however, it is incorporated in one or more softeners and/or phlegmatizing agents and/or solid carriers and/or low or high boiling solvents. The peroxide compositions not only permit being processed in the form of solutions but also in the form of pastes or putties.

As softeners, phlegmatizing agents or solvents can be used esters such as dialkyl phthalates with an alkyl group of 1 to 10 carbon atoms, and those having ring structures, ethyl acetate, butyl acetate, trialkyl phosphates or triaryl phosphates, hydrophilic solvents such as monohydric or polyhydric alcohols, diethylene or triethylene glycols, particularly ketones and hydroxy or alkoxy ketones such as diacetone alcohol, and hydrophobic solvents such as benzene, toluene, xylene or aliphatic hydrocarbons.

It is recommended that the peroxide composition according to the invention be incorporated in fillers such as clay, calcium carbonate or silica. It may be of advantage to add to the peroxide composition flame or fire retarding or suppressing agents, and stabilizers such as mono or dipicolinic acid, pyrophosphates, aluminium compounds, (poly)ethylene glycol ethers, pyrrolidone, N-methyl pyrrolidone, polyvinyl pyrrolidone, aliphatic or hydroxyaliphatic amines, sequestering or masking agents such as nitrilotriacetic acid, ethylene diaminetetra-acetic acid or salts thereof.

As metal accelerators may be used salts of transition metals such as halides or acylates of cobalt, iron, manganese, vanadium, copper, cerium, tin, silver and mercury, preferably however of cobalt, manganese and vanadium, in amounts of 0.001–0.5% by weight, and preferably of 0.005 to 0.05% by weight of metal, calculated on the unsaturated polyester resin.

The peroxide compositions according to the invention can be obtained by reacting alkyl aldehydes having not more than 20 C-atoms with hydrogen peroxide in a solvent in which both the starting aldehydes and the aldehyde peroxides formed therefrom are soluble in the presence of an acid catalyst, with the water being removed during the reaction.

The above-described procedure is a safe way of preparing the peroxide composition to be used according to the invention. Moreover, the presence of a colvent increases the reaction speed and consequently shortens the reaction time.

Finally, the presence of the solvent facilitates the removal of the acid catalyst upon completion of the reaction.

As examples of starting aldehydes may be mentioned: n-butyraldehyde, iso-butyraldehyde, dichlooracetaldehyde, phenylacetaldehyde, diethylacetaldehyde, 2,2-dimethyl-3-hydropropanal heptanal, 2-ethylhexanal, 3,3,5-trimethylhexanal, dodecanal and stearylaldehyde.

The preparation is carried out at a temperature in the range of 10° to 50° C. and preferably at 20° to 40° C. The hydrogen peroxide is added as a solution in water with a $H_2O_2$ content of 30-85% by weight, and preferably of 50-70% by weight. The starting aldehyde is used in such an amount that the molar ratio of carbonyl group to $H_2O_2$ is between 1:15 and 1:40, and preferably between 1:16 and 1:25.

As acid catalyst is used a mineral acid such as sulphuric acid, phosphoric acid or nitric acid, a strongly acid ion exchanger or a strong organic acid such as benzene syphonic or toluene sulphonic acid, chloro-substituted acetic acid or formic acid. These catalysts are used in amounts ranging from 0.2-200 mg equivalents per mole aldehyde, and preferably in 2 to 50 mg equivalents. The water formed during the reaction is removed during the reaction by distillation and preferably under reduced pressure or azeotropically while using suitable solvents such as benzene, toluene, butyl acetate or other liquids, which, together with water, form an azeotrope. After the reaction the acid catalyst is removed by washing with an aqueous alkaline solution which contains alkali bicarbonate, alkali hydroxide or alkali carbonate by adding calcium oxide or magnesium oxide or calcium carbonate or magnesium carbonate followed by filtration or just by filtering through an ion exchanger.

It is preferred that after adding a suitable phlegmatizing agent such as dialkyl phthalates, trialkyl phosphates, alkylene glycols, alkylene glycol monoethers or diethers, diethylene glycols, diethylene glycol monoethers or diethers, alkylene glycol or dialkylene glycol monoether esters, high-boiling alcohols such as dodecanol, octyl alcohol or nonyl alcohol, cyclohexanol, diacetone alcohol, hexylene glycol, polyethylene glycol (M.<2000), hexamethylene glycol, 1,4-butylene glycol, neopentyl glycol, 2-pyrrolidone or N-methyl-2-pyrrolidone, the low-boiling solvent used in the preparation is removed, preferably by distillation, provided that this solvent differs from the above-mentioned phlegmatizing agent. The object is to obtain a phlegmatized peroxide composition having an active acid content of 2-12% by weight.

DESCRIPTION OF THE PREFERRED EMBODIMENTS

The invention is further described in the following examples.

Where in these examples mention is made of an unsaturated polyester resin a "standard" unsaturated polyester resin for general purposes is meant, which unsaturated resin is obtained by condensation of 1 mole of maleic anhydride, 1 mole of phthalic anhydride, 1.1 moles of ethylene glycol and 1.1 moles of propylene glycol to an acid number of about 35, followed by adding 35 parts by weight of styrene to 65 parts by weight of the condensate thus obtained. The resulting unsaturated polyester monomer mixture is subsequently stabilized by adding 0.012 parts by weight of hydroquinone.

By gel time is to be understood the time elapsed between adding a peroxide composition according to the invention and the aforedescribed unsaturated polyester resin to which an accelerator has been added.

EXAMPLE 1

To 50 g of diisobutyl phthalate were added 2.5 g of a strongly acid ion exchanger (Dower 50 W; 4 mg eq. acid per g substance) and 53.6 g of a 70% by weight-hydrogen peroxide solution (1.1 moles). The reaction flask was rinsed with nitrogen. Subsequently, 60.4 g of heptanal (purity 94.3%) (0.5 moles) were added over a period of 15 minutes.

During adding and for 1 hour after stirring the temperature was kept at 20° C. by cooling.

Next, the reaction flask was connected to a vacuum system and water was slowly distilled off from the reaction mixture at 20° C. In 4 hours 31 g of water containing 6.8 of $H_2O_2$ were distilled off along with 1 g of aldehyde.

After the ion exchanger had been removed by filtration, 136 g of peroxide solution were obtained with a total AO content of 10.6%. After mixing with 100 ml of hexane at 0° C. the 7,10-dihydroperoxide-8,9-dioxahexadecane crystallized out and had a melting point of 61°-62° C.:AO content 15.8%; purity 97% (D.L.C.). the infrared absorption spectrum showed a strong band at 3438 $cm^{-1}$, which is attributable to O—O—H.

100 g of the above-mentioned peroxide solution with an AO content of 10.6% were diluted with 71 g of diethylene glycol, resulting in a solution with an AO content of 6.2%. Likewise, solutions were prepared of 1,1,6,6-tetrachloro-2,5-dihydroperoxide-3,4-dioxahexane starting from dichloroacetaldehyde, of 3,8-diethyl-4,7-dihydroperoxy-5,6-dioxadecane starting from diethylacetaldehyde and of 2,2,7,7-tetramethyl-3,6-dihydroperoxy-4,5-dioxa-1,8-octane diol starting from 2,3-dimethyl-3-hydroxypropanol.

EXAMPLE 2

To a solution of 0.3 g of p-toluene sulphonic acid in 60 ml of toluene were added 14.6 g of 70% by weight - hydrogen peroxide solution (0.3 moles) and subsequently, with stirring while keeping the temperature at 20° C. by cooling, 27.6 g of dodecanal (0.15 moles). During adding a white precipitate was formed.

Next, the reaction vessel containing the reaction mixture was connected to a vacuum system and heated to 40° C., at which temperature water was slowly removed by an azeotropic distillation. After 30 minutes a clear solution was formed and in 3½ hours 9 ml of water was obtained containing 13.6% of active oxygen. The dry peroxide solution thus obtained had an AO content of 3.94% and was cooled to −10° C. After the precipitated crystalline product had been isolated by filtration and dried, 29.3 g of 12,15-dihydroperoxy-13,14-dioxahexacosane were obtained with a melting point of 55°-58° C. and an AO content of 10.7% (calculated:11.6%). Purity 97%. According to D.L.C. analysis no other peroxides were present. The infrared absorption spectrum showed a strong band at 3438 $cm^{-1}$, which is attributable to O—O—H. 89 g of the abovementioned peroxide solution in toluene were washed until free of acid with an aqueous sodium bicarbonate solution.

12 g of dimethyl phthalate and 12 g of methoxyethoxyethanol (methyl oxitol) were added, after which the toluene was removed at reduced pressure. Of this peroxide a solution was left in a mixture of dimethyl phthalate and methyl oxitol with an AO content of 6.3%.

EXAMPLE 3

To a mixture of 250 ml of n-butyl acetate, 2,8 g of p-toluene sulphonic acid 1 aq. and 53.5 g of a 70% by weight - hydrogen peroxide solution (1.1 moles) were added, with stirring, 36 g (0.5 moles) of isobutyraldehyde over a period of 15 minutes at 20° C. (cooling).

After 1 hour at 20° C. the reaction flask was evacuated with slow azeotropic distillation at 35° C. In 3 hours 25 ml of water containing about 5.6% hydrogen peroxide were removed from the reaction mixture. The reaction mixture was cooled to 20° C. and the peroxide solution was subsequently washed with a concentrated ammonium sulphate solution and with an 8% by weight sodium carbonate solution. To the resulting solution (about 290 g) were added 100 g of dimethyl phthalate and 40 g of hexylene glycol, which after removal of butyl acetate by distillation under reduced pressure yielded about 210 g of peroxide solution containing 8.0% of active oxygen. By D.L.C. analysis it was shown that about 85% of the AO content was in the form of the dihydroperoxide 2,7-dimethyl-3,6-dihydroxyperoxy-4,5-dioxaoctane. In the same way solutions were prepared of 4,7-dihydoperoxy-5,6-dioxadecane starting from n-butylaldehyde, of 1,6-diphenyl-2,5-dihydroperoxy-3,4-dioxahexane starting from phenylacetaldehyde, of 7,10-dihydroperoxy-8,9-dioxahexadecane starting from heptanal, of 5,10-diethyl-6,9-dihydroperoxy-7,8-dioxatetradecane starting from 2-ethylhexanal, and of 2,4,4,11,11,13-hexamethyl-6,9-dihydroperoxy-7,8-dioxatetradecane starting from 3,3,5-trimethyl hexanal.

EXAMPLE 4

To 100 parts by weight of the afore-described "standard" unsaturated polyester resin were added 0.5 parts by weight of a solution of cobalt octoate in xylene, containing 1% by weight of cobalt and 2.4 parts by weight of a peroxide composition which contained a bis(1-hydroperoxyalkyl) peroxide with 1½ atoms of active oxygen per starting aldehyde. Of the mixture the gel time at 20° C. and the Persoz hardness were determined after 1, 2, 4 and 6 hours.

Corresponding measurements were carried out on a mixture containing the same accelerator and the same peroxide, although in different amounts. The same measurements were carried out on mixtures containing the same accelerator but different peroxide compositions according to the invention. The used peroxide compositions according to the invention and the mixtures prepared, and the gel times and the hardness values are shown in the following table.

For comparison the bis(1-hydroxyheptyl) peroxide with an active oxygen content of 6.1% by weight (peroxide P) is included in the table.

| Peroxide | derived from | Act. 0-content in & by wt |
|---|---|---|
| A | n-butylraldehyde | 8.64 |
| B | iso-butylraldehyde | 6.43 |
| C | phenylacetaldehyde | 6.90 |
| D | heptanal | 7.30 |
| E | dodecanal | 10.70 |

TABLE I

| RESIN | 100 | 100 | 100 | 100 | 100 | 100 | 100 | 100 | 100 | 100 | 100 | 100 |
|---|---|---|---|---|---|---|---|---|---|---|---|---|
| Cobalt accelerator | 0.5 | 1.0 | 0.5 | 1.0 | 0.5 | 1.0 | 0.5 | 1.0 | 0.5 | 1.0 | 0.5 | 1.0 |
| A | 2.4 | 1.2 | — | — | — | — | — | — | — | — | — | — |
| B | — | — | 3.3 | 1.6 | — | — | — | — | — | — | — | — |
| C | — | — | — | — | 3.0 | 1.5 | — | — | — | — | — | — |
| D | — | — | — | — | — | — | 2.88 | 1.44 | — | — | — | — |
| E | — | — | — | — | — | — | — | — | 2.0 | 1.0 | — | — |
| P | — | — | — | — | — | — | — | — | — | — | 3.4 | 1.7 |
| Gel time (min.)20° C. | 29 | 33 | 41 | 55 | 28 | 29 | 32 | 49 | 14 | 18 | 5 | 4 |
| Persoz hardness | | | | | | | | | | | | |
| after 1 hour | 63 | 31 | 41 | — | 56 | 41 | 40 | 39 | 118 | 37 | 102 | 78 |
| after 2 hours | 91 | 69 | 106 | 88 | 84 | 71 | 86 | 54 | 137 | 89 | 125 | 112 |
| after 4 hours | 123 | 114 | 140 | 128 | 112 | 103 | 115 | 112 | 156 | 123 | — | — |
| after 6 hours | 129 | 127 | 152 | 141 | 132 | 120 | 132 | 128 | 162 | 143 | 170 | 152 |

EXAMPLE 5

To 100 parts by weight of the afore-described "standard" unsaturated polyester resin were added 0.5 parts by weight of the cobalt octoate solution described in Example 4 and 2.5 parts by weight of a peroxide composition according to the invention, which contained an alkyl aldehyde peroxide with 2 atoms of active oxygen per starting aldehyde.

Of the mixture the gel time at 20° C. and the Persoz hardness after 1, 2, 4 and 6 hours were determined. Corresponding measurements were carried out on a mixture, which contained the same accelerator and the same peroxide, although in different quantities. The same measurements were carried out on mixtures containing the same accelerator but different peroxide compositions according to the invention.

The used peroxide compositions according to the invention and the prepared mixtures, the gel times and the hardness values are given in the following table. For comparison the bis(1-hydroxy-2-phenylethyl) peroxide with an active oxygen content of 5.84% by weight (peroxide Q) is included in the table

| Peroxide | berived from | Act. 0-content in wt % |
|---|---|---|
| F | n-butylaldehyde | 8.26 |
| G | phenylacetaldehyde | 6.58 |
| H | heptanal | 6.95 |
| J | isobutylraldehyde | 5.60 |
| K | 2-methylpentanol | 10.78 |

Table II

| RESIN | 100 | 100 | 100 | 100 | 100 | 100 | 100 | 100 | 100 | 100 | 100 | 100 |
|---|---|---|---|---|---|---|---|---|---|---|---|---|
| Cobalt accelerator | 0.5 | 1.0 | 0.5 | 1.0 | 0.5 | 1.0 | 0.5 | 1.0 | 0.5 | 1.0 | 0.5 | 1.0 |
| F | 2.5 | 1.25 | — | — | — | — | — | — | — | — | — | — |
| G | — | — | 3.2 | 1.6 | — | — | — | — | — | — | — | — |
| H | — | — | — | — | — | — | — | — | — | — | — | — |
| J | — | — | — | — | — | — | 3.75 | 1.88 | — | — | — | — |

Table II-continued

|   | | | | | | | | | | | | | |
|---|---|---|---|---|---|---|---|---|---|---|---|---|---|
| K | — | — | — | — | — | — | — | — | 1.95 | 0.97 | — | — | |
| Q | — | — | — | — | — | — | — | — | — | — | 3.6 | 1.8 | |
| Gel time in min. 20° C. | 18 | 19 | 15 | 14 | 16 | 16 | 13 | 16 | 16 | 13 | 7 | 4 | |
| Persoz hardness | | | | | | | | | | | | | |
| after 1 hour | 62 | 58 / 93 | 93 | 52 | 58 | 50 | 89 | 65 | 114 | 92 | 79 | | |
| after 2 hours | 85 | 82 | 115 | 112 | 73 | 80 | 69 | 109 | 83 | 128 | 109 | 101 | |
| after 4 hours | 115 | 115 | 127 | 126 | 119 | 113 | 104 | 138 | 111 | 141 | 137 | 128 | |
| after 6 hours | 133 | 131 | 148 | 150 | 127 | 129 | 124 | 152 | 122 | 168 | 148 | 143 | |

EXAMPLE 6

To 100 parts by weight of the afore-described "standard" unsaturated polyester resin were added 0.5 parts by weight of the cobalt solution described in Example 4 and 1.33 parts by weight of a peroxide composition according to the invention, which in addition to an alkylaldehyde peroxide with 1½ atoms of active oxygen contained an alkylaldehye peroxide with 2 atoms of active oxygen per starting aldehyde. Of the mixture the gel time at 20° C. and the Persoz hardness after 1, 2, 4 and 6 hours were determined.

Corresponding measurements were carried out as described in Examples 4 and 5. The used peroxide compositions according to the invention and the prepared mixtures, the gel times and the hardness values are listed in the following table (TABLE III)

| Peroxide | Derived from | Act. O-content in wt % total | 1½ | 2 |
|---|---|---|---|---|
| L | heptanal | 7.90 | 3.00 | 4.90 |
| M | heptanal | 5.50 | 2.90 | 2.60 |
| N | diethylacetaldehyde | 9.40 | 5.00 | 4.40 |
| O | 2,2-dimethyl-3-hydroxy propanal | 4.50 | 1.80 | 2.70 |

The cured unsaturarted polyester/monomer mixture thus obtained can be used e.g. for the manufacture of casings for refrigerators, automobile parts, articles for the electronic industry, glass reinforced pipes, drains, tanks and the like.

TABLE III

| RESIN | 100 | 100 | 100 | 100 | 100 | 100 | 100 | 100 | 100 | 100 | 100 | 100 | 100 | 100 |
|---|---|---|---|---|---|---|---|---|---|---|---|---|---|---|
| Cobalt accelerator | 0.5 | 1.0 | 0.5 | 1.0 | 0.5 | 1.0 | 0.5 | 1.0 | 0.5 | 1.0 | 0.5 | 1.0 | 0.5 | 1.0 |
| L | 1.33 | 2.66 | — | — | — | — | — | — | — | — | — | — | — | — |
| M | — | — | 1.9 | 3.8 | — | — | — | — | — | — | — | — | — | — |
| N | — | — | — | — | 1.1 | 1.1 | 2.2 | — | — | — | — | — | — | — |
| O | — | — | — | — | — | — | — | 2.3 | 2.3 | 4.7 | — | — | — | — |
| P | — | — | — | — | — | — | — | — | — | — | 3.4 | 1.7 | — | — |
| Q | — | — | — | — | — | — | — | — | — | — | — | — | 3.6 | 1.8 |
| Gel time in min. 20° C. | 13 | 18 | 20 | 12 | 14 | 17 | 14 | 18 | 15 | 15 | 5 | 4 | 7 | 4 |
| Persoz hardness | | | | | | | | | | | | | | |
| after 1 hour | 35 | 56 | 35 | 46 | 49 | 70 | 76 | 40 | 60 | 54 | 102 | 78 | 92 | 79 |
| after 2 hours | 52 | 76 | 42 | 76 | 71 | 93 | 98 | 61 | 79 | 76 | 125 | 112 | 108 | 101 |
| after 4 hours | 81 | 105 | 83 | 104 | 99 | 125 | 121 | 83 | 104 | 97 | — | — | 137 | 128 |
| after 6 hours | 102 | 122 | 99 | 127 | 118 | 128 | 96 | 96 | 113 | 110 | 170 | 132 | 148 | 143 |

What is claimed is:

1. A process for preparing an alkylaldehyde peroxide containing not more than 20 carbon atoms and at least 1.5 active oxygen atoms per carbonyl group of alkylaldehyde, said alkylaldehyde peroxide being selected from the group consisting of unsubstituted alkylaldehyde peroxide, alkyl-substituted alkylaldehyde peroxide, and aryl-substituted alkylaldehyde peroxide, comprising reacting an alkylaldehyde with not more than 20 carbon atoms with hydrogen peroxide in the form of an aqueous solution having an $H_2O_2$ content between about 30 and about 85% by weight, in a solvent in which both the alkylaldehyde and the formed peroxide composition are soluble, the molar ratio of carbonyl groups to $H_2O_2$ is the reaction mixture being between 1:1.5 and 1:4.0, in the presence of an acid catalyst with the simultaneous removal of water by distillation.

2. The process of claim 1 in which said acid catalyst is selected from the group consisting of a mineral acid, a strongly acid ion exchanger, and a strong organic acid.

3. The process of claim 2 in which said acid catalyst is employed in an amount of 0.2 to 200 mg equivalent per mole of aldehyde.

4. The process of claim 1 in which the reaction water is removed by distillation under reduced pressure.

5. The process of claim 1 in which the reaction water is distilled off in the presence of an organic solvent which forms an azeotrope with water.

6. The process of claim 5 in which said organic solvent is a member of the group consisting of benzene, toluene, and butyl acetate.

7. The process of claim 1 in which said reaction is carried out at a temperature between about 10° and about 50° C.

8. An alkylaldehyde peroxide containing not more than 20 carbon atoms and at least 1.5 active oxygen atoms per carbonyl group of alkylaldehyde, said alkylaldehyde peroxide being selected from the group consisting of unsubstituted alkylaldehyde peroxide, alkyl-substituted alkylaldehyde peroxide, and aryl-substituted alkylaldehyde peroxide, prepared by reacting an alkylaldehyde with not more than 20 carbon atoms with hydrogen peroxide in the form of an aqueous solution having an $H_2O_2$ content between about 30 and about 85% by weight, in a solvent in which both the alkylaldehyde and the formed peroxide composition are soluble, the molar ratio of carbonyl groups to $H_2O_2$ in the reaction mixture being between 1:1.5 and 1:4.0, in the presence of an acid catalyst with the simultaneous removal of water by distillation.

* * * * *